United States Patent
Kumar et al.

(10) Patent No.: US 7,371,902 B2
(45) Date of Patent: May 13, 2008

(54) METHODS FOR PURIFYING P,P-BISPHENOL-A

(75) Inventors: Ramachandran Kumar, Bangalore (IN); Gomatam Raghavan Ravi, Bangalore (IN); Hyacinth Mary Bastian, Bangalore (IN); Gururaj Sathyanarayana, Bangalore (IN); Sheldon Jay Shafer, Clifton Park, NY (US); Kumar Krishna Ramamurthy, Bangalore (IN); Dwijaraja Mouli Murukutla, Bangalore (IN); Venkata Rama Narayanan Ganapathy Bhotla, Puram Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/953,132

(22) Filed: Sep. 29, 2004

(65) Prior Publication Data
US 2006/0069292 A1    Mar. 30, 2006

(51) Int. Cl.
*C07C 37/68* (2006.01)
*C07C 39/12* (2006.01)
*C07C 39/16* (2006.01)

(52) U.S. Cl. .................. 568/724; 568/722; 568/723
(58) Field of Classification Search ............... 568/724, 568/728
See application file for complete search history.

(56) References Cited
U.S. PATENT DOCUMENTS

| 4,192,954 | A | * | 3/1980 | Barker et al. ............... 568/723 |
| 4,822,923 | A | * | 4/1989 | Li ............................... 568/724 |
| 4,825,010 | A | * | 4/1989 | Li ............................... 568/724 |
| 5,198,591 | A | | 3/1993 | Kiedik et al. |
| 5,300,700 | A | | 4/1994 | Malamet et al. |
| 5,696,295 | A | * | 12/1997 | Wulff et al. ................ 568/724 |
| 5,723,689 | A | | 3/1998 | Pressman et al. |
| 5,785,823 | A | | 7/1998 | Meurer et al. |
| 6,294,702 | B1 | * | 9/2001 | Fennhof et al. ............ 568/727 |
| 6,414,198 | B1 | | 7/2002 | Lanze et al. |
| 6,414,199 | B1 | | 7/2002 | Saruwatari |
| 6,459,004 | B1 | * | 10/2002 | Ono et al. .................. 568/728 |

FOREIGN PATENT DOCUMENTS

| BE | 678 415 A | 9/1966 |
| EP | 0 552 518 A1 | 7/1993 |

\* cited by examiner

*Primary Examiner*—Karl Puttlitz

(57) ABSTRACT

Methods for purifying a p,p-bisphenol A generally include distilling a feed stream comprising p,p-BPA in a distillation column at a pressure less than or equal to 20 millibars. The distillation column separates the bisphenol feed stream to produce a light fraction, an intermediate fraction and a heavy fraction. The intermediate fraction comprising the purified bisphenol contains lesser impurities that the p,p-BPA in the feed stream. In one embodiment, the intermediate stream is recovered using a side-draw. The side-draw is located between a first zone and a third zone in the distillation column.

20 Claims, 1 Drawing Sheet

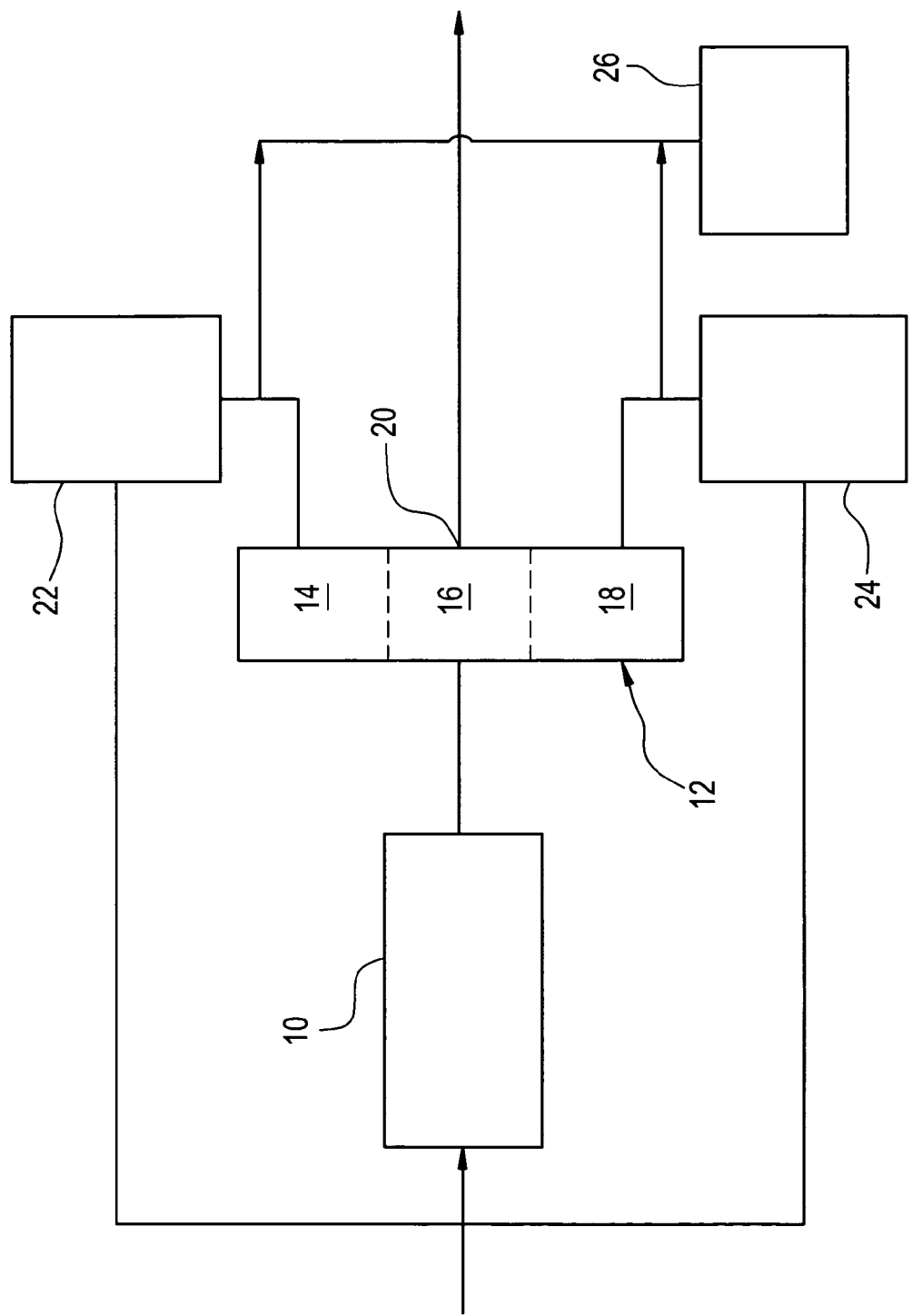

METHODS FOR PURIFYING P,P-BISPHENOL-A

BACKGROUND

The present disclosure relates to a method for the purification of bisphenol A. More particularly, the disclosure relates to an economical method and apparatus for the purification of para, para-bisphenol-A.

The compound, para, para-bisphenol A (hereinafter referred to as p,p-BPA) has been previously prepared, for example from acetone and phenol in the presence of an acid catalyst according to methods known in the art. The p,p-BPA prepared in this manner generally comprises the ortho isomer of bisphenol-A, generally referred to as ortho, para-bisphenol-A (hereinafter referred to as o,p-BPA), unreacted phenol, isopropenyl phenol (hereinafter referred to as IPP), 2,4-Bis[2-(4-hydroxyphenyl)propyl]phenol (hereinafter referred to as BPX-1), 4-[1-methyl-1-{2,2,4-trimethyl-4-(p-hydroxyphenyl)-chroman-6-yl}-ethyl]-phenol (hereinafter referred to as BPX-II), 4-(2,2,4-trimethyl-chroman-4-yl)-phenol (chroman 1.0) and 4-(2,4,4-trimethyl-chroman-2-yl)-phenol (chroman 1.5), (hereinafter collectively referred to as chromans) and dimers. The p,p-BPA prepared in this manner may be suitable, without further purification, for use as a monomer unit for the preparation of other polymers, for example, polycarbonates.

However, if the polymers prepared from bisphenol-A are to be of a particular purity, the purity of the bisphenol-A monomer would need to match these requirements. For relatively pure polymers, the purity required of p,p-BPA is generally about 99.5 to about 99.9%. Presently, to get these required purities, bisphenols obtained in the manner described above are further purified, for example, by melt crystallization of the bisphenol monomer or by adduct formation with the phenol and subsequent removal of the phenol. However, these additional purification steps are relatively costly. Alternatively, bisphenol A/phenol adducts with less than 10% isomers and phenol have been purified by fractionating under vacuum and distillation, with the successive separation of high-boiling, low-boiling, and undistilled components to provide highly pure bisphenol-A. However, as noted, successful use of this method requires a relatively pure starting material to obtain highly pure p,p-BPA, e.g., less than 10% isomers.

Thus, what is needed is a more robust method for obtaining pure p,p-BPA. Preferably, the method is economically practical and permits the use of a bisphenol feed stream from any source, such as for example, a product stream from a bisphenol-A process, impure bisphenol flakes and others.

BRIEF DESCRIPTION

Disclosed herein are methods for purifying a p,p-bisphenol-A. In one embodiment, the method comprises, distilling a feed stream comprising p,p-BPA in a distillation column at a pressure less than or equal to 20 millibars. In the distillation system the bisphenol feed stream is separated to produce a first zone comprising a light fraction, a second zone comprising an intermediate fraction and a third zone comprising a heavy fraction. The intermediate fraction comprising the purified bisphenol contains lesser impurities than the p,p-BPA in the feed stream. The intermediate stream is recovered using a side-draw. The side-draw is located between the first zone and the third zone in the distillation column.

In another embodiment, the method for purifying a feedstream comprising p,p-bisphenol A comprises flowing the feedstream comprising p,p-bisphenol A into a distillation column. The distillation column comprises a first zone, a third zone, and a second zone intermediate the first and third zones. Flowing the feedstream comprises, introducing the feedstream into the second zone; distilling the feedstream into three fractions, wherein a light fraction is produced from the first zone, an intermediate fraction is produced from the second zone and a heavy fraction is produced from the third zone. The intermediate fraction comprises p,p-bisphenol A at a purity greater than 90% and at a purity greater than the p,p-bisphenol A in the feedstream.

BRIEF DESCRIPTION OF THE DRAWINGS

The Figure is a flow chart for producing purified p,p--bisphenol A in accordance with the present disclosure.

DETAILED DESCRIPTION

The FIGURE graphically illustrates a method for producing purified para, para bisphenol-A. The process generally comprises purifying a p,p-BPA monomer containing feedstream 10 such as may be produced from the acid catalyzed reaction of phenol and acetone or the like. Although the method disclosed herein is particularly well suited for purifying p,p-BPA produced by the acid catalyzed reaction of phenol and acetone, the method can also be used to purify p,p-BPA obtained from diverse sources. For example, a suitable p,p-BPA feed stream for purification may comprise p,p-BPA and phenol obtained from a bisphenol manufacturing process or p,p-BPA used as a raw material for other manufacturing processes to produce polymers; non-limiting examples of which include polycarbonates or may comprise a bisphenol melt prepared from bisphenol flakes of lesser purity. In one embodiment, the p,p-BPA feed stream comprises greater than or equal to 80% by weight of p,p-BPA based on the other components present in the stream. The other components generally can comprise o,p-BPA, IPP, BPX-1, BPX-II, chromans, as well as linear and cyclic dimers.

In one embodiment, the p,p-BPA monomer containing feedstream 10 is fed to distillation column 12, which generally consists of at least three zones 14, 16, and 18. The p,p-BPA monomer containing feedstream 10 is fed at about a middle of the column 12. The different zones generally function to separate the p,p-BPA monomer containing feedstream into three fractions. A light fraction is produced from zone 14, an intermediate fraction is produced from zone 16, and a heavy fraction is produced from zone 18. In one embodiment 5% to 20% of the feedstream is withdrawn as the light fraction, 60% to 90% of the feedstream is withdrawn as the intermediate fraction and 5% to 20% of the feedstream is withdrawn as the heavy fraction. Typically, the light fraction has a higher vapor pressure than the intermediate fraction and the intermediate fraction has a higher vapor pressure than the heavy fraction. The distillation column is typically a vertical distillation column wherein the at least three zones are distributed in vertical manner. Generally, the pressure and temperature in zone 14 and 16 are measured at the top of the zone and the pressure and temperature in zone 18 are measured at the bottom of the zone.

Optionally, the distillation column comprises a plurality of stages that define the various zones 14, 16, and 18, and functions as a rectification column. The number of theoretical stages is generally from 4 to 30 stages, and in some embodiments, the number of stages is 10 to 15. In other embodiments, the number of theoretical stages is 12 to 13 stages.

The pressure maintained in the different zones in the distillation column 12 is such that the corresponding temperature in the different zones in the distillation column 12 can be maintained at a value, wherein the loss of p,p-BPA due to decomposition in any of the first, second, or third zones is minimized and/or prevented. Typically the pressure in the zone 14 is maintained at less than or equal to 15 millibars. In another embodiment, the pressure in zone 14 is less than or equal to 7 millibars. In still other embodiments, the pressure in zone 14 is less than or equal to 3.5 millibars. Typically, the temperature in the zone 14 is maintained at 170 to 230° C. In another embodiment, the temperature in zone 14 is 180 to 220° C. In still other embodiments, the temperature in zone 14 is maintained at 195 to 210° C. The light fraction that is withdrawn from zone 14 can generally comprise 30% to 90% p,p-BPA, 0% to 20% o,p-BPA, 0% to 20% IPP, 0% to 20% chromans and 0% to 20% phenol. The light fraction may be withdrawn in a liquid phase, vapor phase, or a vapor-liquid phase.

The intermediate fraction that is withdrawn from the zone 16 comprises the purified p,p-BPA. The pressure maintained in zone 16 is generally less than or equal to 15 millibar, more specifically less than or equal to 10 millibar, and even more specifically, less than or equal to 5 millibars. Operating under this pressure regime helps to maintain a temperature range which provides a liquid phase effluent of p,p-BPA without any measurable degree of decomposition. Typically, the temperature in zone 16 is maintained at 210 to 230° C. In one embodiment the temperature in zone 16 is 212 to 225° C. In still other embodiments, the temperature in zone 16 is 215 to 220° C.

In practice, the intermediate fraction is withdrawn from distillation column 12 as a so called "side-draw". That is, the intermediate fraction is obtained from about the middle of column 12. In the figure, the side-draw is designated 20 and may be located anywhere in the intermediate zone between zone 14 and zone 18. In an exemplary distillation column configured with twelve stages, the side-draw 20 may be located at the second to seventh theoretical stage from the top, and even more specifically, at the third to fourth theoretical stage from the top of distillation column 12. The intermediate fraction comprises p,p-BPA with greater than or equal to 90% purity. In one embodiment, the intermediate fraction comprises p,p-BPA with greater than or equal to 99.96% purity.

The heavy fraction is withdrawn from the bottom of the distillation column 12 and generally comprises 50% to 95% p,p-BPA, 0% to 20% o,p-BPA, 0% to 20% BPX-I, 0% to 20% BPX-II and 0% to 30% dimers. The pressure and temperature at the bottom of zone 18 is maintained such that there is zero or minimal degradation and a liquid phase effluent is obtained. The pressure is generally less than or equal to 20 millibar, more specifically the pressure is less than or equal to 13 millibar, and even more specifically, the pressure is less than or equal to 11 millibar. In one embodiment, the temperature in zone 18 is at 200 to 300° C. In another embodiment the temperature in zone 18 is at 230 to 290° C. In still other embodiments, the temperature in zone 18 is at 240 to 255° C.

The pressures defined above in the different zones are maintained to achieve the separation of the bisphenol feed stream in the three zones. The temperature in the three zones varies according to the pressure utilized therein as will be appreciated by those skilled in the art. The pressure and temperature are maintained in the various zones such that separation into three different fractions is achieved and degradation is minimized. Typically, as described above, the pressure in zone 14 maintained at less than or equal to 15 millibars and the temperature in zone 14 is maintained at 170 to 230° C. Typically, the pressure in zone 16 is maintained at less than or equal to 15 millibar and the temperature in zone 16 is maintained at 210 to 230° C. Typically, the pressure in zone 18 is maintained at less than or equal to 20 millibar and the temperature is maintained at 200 to 300° C.

The light fraction may then be optionally fed into a reactor 22 (at times referred to as light reactor or first reactor) having an acid catalyst therein. Without being bound to theory, it is believed that the acid catalyst isomerizes the o,p-BPA in the light fraction to p,p-BPA whereas the IPP that may be present in the light fraction may react with unreacted phenol contained in the light fraction feedstream to form additional p,p-BPA in the presence of the acid catalyst. To facilitate isomerization, the reactor 22 is maintained at 40 to 150° C.; in another embodiment, the temperature is maintained at 45 to 100° C.; and in still other embodiments, the temperature is maintained at 50 to 75° C. The effluent from reactor 22 can be fed back to the distillation column 12 and further processed as previously described.

Likewise, the heavy fraction may optionally be fed to reactor 24 (at times referred to as heavy reactor or second reactor), which contains the same and/or a different acid catalyst as in reactor 22. It is believed that the o,p-BPA, BPX-I and BPX-II that may be in the heavy fraction is isomerized to p,p-BPA in presence of the acid catalyst in reactor 24 to generate an effluent stream from reactor 24, which can subsequently be fed back to distillation column 12 for isolation of p,p-BPA. In one embodiment, the temperature that is maintained in the reactor 24 to facilitate isomerization is 40 to 180° C.; in another embodiment, the temperature is 45 to 100° C.; and in still other embodiments, the temperature is 50 to 75° C. The effluent from reactor 24 can be fed back to the distillation column 12 and further processed as previously described.

Still further, a solvent may optionally be added to one or both heavy and light reactors 24, 22, respectively. The solvent provides a viscosity to the heavy fraction and light fraction effective to maintain a flowing consistency. The solvents that may be used to maintain the flow comprise solvents containing one to twelve carbon atoms. More specifically, the solvents may be selected form the group consisting of but not limited to inert solvents, for example, toluene, cyclohexane; aliphatic alcohols, for example methanol, ethanol; aromatic hydroxy compounds, for example phenol; and chlorinated solvents, for example, ortho dichlorobenzene. In one embodiment, the solvent used is phenol. Phenol is a preferred solvent since it is already present as a reactant and the use of additional distillation columns to remove any other solvent if employed, can be avoided.

Suitable acid catalysts for use in reactors 22 and 24 include, but are not intended to be limited to, hydrochloric acid, cation exchange resins in the hydrogen form such as sulphonated styrene divinylbenzene catalysts. For example, a suitable acid catalyst is available under the tradename Amberlyst™ 31Wet, or higher performing monodisperse catalysts like Amberlyst™ 121Wet, 131Wet and 232Wet, which are commercially available from Rohm and Hass and k1131 resin commercially available from Bayer and.

Optionally, a make-up quantity of phenol may also be fed to reactors 22 and/or 24. Generally, the amount of make-up phenol added is such that 50 to 85% of the overall composition of feedstream entering reactors 22 and/or 24 is phenol. Optionally, the resulting feedstream (effluent) from reactors 22 and/or 24 may initially be subjected to phenol, o,p-BPA and chromans removal as may generally be carried out during the acid catalyzed reaction of acetone and phenol, and then fed to the distillation column 12 for further processing to obtain additional p,p-BPA. In addition to the added phenol functioning as a solvent, it is believed that in the lights reactor phenol reacts with IPP to provide additional p,p-BPA and also facilitates the isomerization reactions both in the light and heavy reactors. Optionally, 0 to 50% of the light fraction and/or heavy fraction may be purged to prevent build up of impurities in the purification process. For example, chromans can build up in the case of the light fraction and dimers and BPX-II can build up in the case of the heavy fraction. The build up of these impurities can decrease the effectiveness of the distillation column 12 and hence subsequently effect the purity of the intermediate fraction. The term "purged" generally infers that about 0 to 50% of the stream that is being fed to the light or heavy reactor from distillation column 12 is diverted to a third reactor, reactor 26 and treated as discussed below. In one embodiment, purging occurs subsequent to distillation and prior to isomerization in reactors 22, 24.

The optional purge streams from the light and/or heavy fractions can be directed to a reactor 26 as mentioned above, which functions as a tar cracker. Effluent from reactor 26 containing phenol and IPP may then be withdrawn and reused in the manufacture of p,p-BPA as previously described. Under the catalytic conditions maintained in the tar cracker, either phenol and IPP or only phenol, may be recovered from the purge streams. When an acidic catalyst is used in the tar cracker, phenol can be recovered. Typically, the acidic catalyst used comprises aromatic sulfonic acid, for example dodecyl benzene sulfonic acid (DBSA). When a basic catalyst is used in the tar cracker, phenol and IPP can be recovered. Typically the basic catalyst used comprises alkali metal hydroxides, for example, sodium hydroxide, potassium hydroxide; and alkali metal carbonates, for example, potassium carbonate.

Surprisingly, the use of the side-draw mechanism to withdraw the intermediate fraction provides p,p-BPA at a purity of 99.5% to 99.9%, irrespective of the source of p,p-BPA employed. Without being bound to theory it is believed that withdrawing p,p-BPA as a side-draw in the liquid phase, minimizes the creep of light impurities and degradation impurities into the final product. Also, recycling of the light fractions after passing through reactor 22 as well as the heavy fraction after passing through reactor 24 increases the throughput and yield of p,p-BPA by 5% to 10%.

Experimental Section

High performance liquid chromatography (HPLC) method was used to check the level of impurities in p,p-BPA withdrawn as the intermediate fraction. The column used was a commercially available Phenomenex Luna C18(2) (4.6×150 mm), 5 microns reverse phase column available from Shimadzu. The detector wavelength was at 235, 250, 280 and 290 nanometers. The mobile phase consisted of a ternary gradient system with water, methanol and acetonitrile mixture in a 90:1:9 volume ratio.

EXAMPLE 1

A distillation column of 6 meters total packed height of Sulzer BX type structured packing was used with a partial condenser located at stage 1 (i.e., zone 14 as shown in the Figure). The bisphenol feed stream was introduced at the $9^{th}$ stage (located at 3.6 m packed height from the column top). The intermediate fraction 3 (the product stream) was withdrawn from a side-draw located at $3^{rd}$ stage (i.e., zone 16). The zone 18 was located at $12^{th}$ stage (located at 0.6 m packed height from the column top) and the heavy fraction was withdrawn from this zone. The convention followed is that all the trays are numbered starting from the top. The temperature, pressure, and flow conditions at the zones of light fraction zone 14, intermediate zone 16 and heavy fraction zone 18 are included in Table I below. Table I also includes the feed conditions and composition of feed, lights fraction, intermediate fraction, heavy fraction and the other streams.

TABLE 1

| | Stream No. | | | | | | | | |
|---|---|---|---|---|---|---|---|---|---|
| | 1 | 2 | 3 | 4 | 5 | 6 | 7 | 8 | 9 |
| Stream Names | Bisphenol feed stream | Light Fraction | Intermediate Fraction (PRODUCT) | Heavy Fraction | Light Purge to Tar Cracker | Heavy Purge to tar cracker | Heavy Reactor to distillation Column | Light Reactor to distillation column | Top product of tar cracker |
| Temperature °C. | 247 | 194 | 217 | 246 | 170 | 223 | 65 | 65 | 88 |
| Pressure millibar | 15 | 1 | 4 | 11 | 5 | 11 | 2000 | 2000 | 20 |
| Mass Flow kg/hr | 10000 | 545 | 8639 | 816 | 166 | 574 | 2041 | 3629 | 395 |
| PHENOL | ND | 8 | ND | ND | 9 | 3 | 80 | 75 | 50 |
| WATER | ND | ND | ND | ND | ND | ND | ND | ND | ND |
| ACETONE | ND | ND | ND | ND | ND | ND | ND | ND | ND |
| p,p-BPA | 97 | 80 | 99.85 | 69 | 34 | 59 | 15 | 22 | ND |
| o,p-BPA | ND | 1 | ND | ND | 45 | 13 | ND | 2 | ND |
| CHROMANS | ND | ND | ND | ND | 2 | 1 | ND | ND | ND |
| Dimer-1 | ND | ND | ND | 3 | ND | 2 | ND | ND | ND |
| BPX-I | 1 | ND | ND | 10 | ND | 7 | 1 | ND | ND |
| BPX-II | 1 | ND | ND | 7 | ND | 5 | 1 | ND | ND |
| TOLUENE | ND | ND | ND | ND | ND | ND | ND | ND | ND |
| Dimer-2 | ND | ND | ND | ND | ND | ND | ND | ND | ND |

TABLE 1-continued

| | Stream No. | | | | | | | | |
|---|---|---|---|---|---|---|---|---|---|
| | 1 | 2 | 3 | 4 | 5 | 6 | 7 | 8 | 9 |
| Dimer-3 | 1 | ND | ND | 11 | ND | 8 | 3 | ND | ND |
| IPP | ND | 10 | ND | ND | 9 | 3 | ND | ND | 50 |

Example 1 indicates how an initial feed stream with 97.35% p,p-BPA is purified to obtain a p,p-BPA with 99.85%. The yield of p,p-BPA obtained was 88.6%. In addition, p,p-BPA was recovered from the light and heavy fraction, thus advantageously increasing the throughput and yield to 96.8%. ND in Table 1 means non detectable. Generally less than 10 ppm of impurities were not detected.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A method for purifying p,p-bisphenol A, said method comprising:
    distilling a feedstream comprising p,p-bisphenol A in a distillation column at a pressure less than or equal to 20 millibars;
    producing a light fraction, an intermediate fraction, and a heavy fraction from the distillation column;
    feeding the heavy fraction to a second reactor and isomerizing impurities in the heavy fraction to produce additional p,p-bisphenol A;
    feeding a portion of the light fraction to a first reactor and purging a remaining portion of the light fraction in a third reactor, wherein feeding the portion to the first reactor converts impurities in the light fraction to produce additional p,p-bisphenol A, and wherein feeding the remaining portion to the third reactor removes impurities from the remaining portion; and
    recovering the intermediate fraction as a side draw of the distillation column, wherein the p,p-bisphenol A in the intermediate fraction contains less impurities than the p,p-bisphenol A in the feedstream.

2. The method of claim 1, wherein said feedstream comprises greater than or equal to 80% p,p-bisphenol A.

3. The method of claim 1, wherein the light fraction is a vapor, a liquid or a vapor-liquid.

4. The method of claim 1, wherein the intermediate and heavy fractions are liquids.

5. The method of claim 1, wherein the first reactor comprises an acid catalyst.

6. The method of claim 1, further comprising introducing phenol into the first reactor.

7. The method of claim 1, further comprising feeding a feedstream containing the additional p,p-bisphenol A produced in the first reactor to the distillation column.

8. The method of claim 1, wherein the third reactor produces an effluent comprising phenol or phenol and isopropenyl phenol.

9. The method of claim 1, wherein the second reactor comprises an acid catalyst.

10. The method of claim 1, further comprising simultaneously feeding a solvent into the second reactor.

11. The method of claim 1, further comprising introducing phenol into the second reactor.

12. The method of claim 1, further comprising feeding a feedstream containing the additional p,p-bisphenol A produced in the second reactor to the distillation column.

13. The method of claim 1, wherein the distillation column comprises 4 to 30 theoretical stages.

14. A method for purifying a feedstream comprising p,p-bisphenol A, comprising:
    flowing the feedstream comprising p,p-bisphenol A into a distillation column, wherein the distillation column comprises a first zone, a third zone, and a second zone intermediate the first and third zones; wherein flowing the feedstream comprises introducing the feedstream into the second zone;
    distilling the feedstream into three fractions, wherein a light fraction is produced from the first zone, an intermediate fraction is produced from the second zone and a heavy fraction is produced from the third zone, wherein the intermediate fraction is withdrawn from the distillation column as a side draw and comprises p,p-bisphenol A at a purity greater than 90% and at a purity greater than the p,p-bisphenol A in the feedstream.

15. The method of claim 14, further comprising:
    flowing the light fraction to a first reactor, wherein the light fraction comprises o,p-bisphenol A and/or isopropenyl phenol; and
    converting the o,p-bisphenol A to form additional p,p-bisphenol A, and/or reacting the isopropenyl phenol with phenol to form the additional p,p-bisphenol A.

16. The method of claim 15, further comprising:
    feeding the additional p,p, bisphenol A to the distillation column.

17. The method of claim 14, further comprising:
    flowing the heavy fraction to a second reactor; and
    isomerizing o,p-bisphenol A, and/or 2,4-bis[2-(4-hydroxyphenyl)propyl]phenol, and/or 4-[1-methyl-1-{2,2,4-trimethyl-4-(p-hydroxyphenyl)-chroman-6-yl}-ethyl]-phenol to form additional p,p-bisphenol A.

18. The method of claim 17, further comprising feeding the additional p,p-bisphenol A to the distillation column.

19. The method of claim 17, further comprising diluting the heavy fraction with a solvent.

20. The method of claim 14, wherein the distillation column is at a pressure less than or equal to 20 millibars, the first zone is at a temperature of 150 to 230° C., the second zone is at a temperature of 210 to 230° C., and the third zone is at a temperature of 200 to 300° C.

* * * * *